US009164022B2

(12) United States Patent
Zhu et al.

(10) Patent No.: US 9,164,022 B2
(45) Date of Patent: Oct. 20, 2015

(54) NEIGHBORHOOD THRESHOLDING IN MIXED MODEL DENSITY GATING

(71) Applicant: Becton, Dickinson and Company, Franklin Lakes, NJ (US)

(72) Inventors: Yuanxin Zhu, Fremont, CA (US); Mengxiang Tang, San Jose, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 14/620,720

(22) Filed: Feb. 12, 2015

(65) Prior Publication Data
US 2015/0160115 A1    Jun. 11, 2015

Related U.S. Application Data

(63) Continuation of application No. 13/053,109, filed on Mar. 21, 2011, now Pat. No. 8,990,047.

(51) Int. Cl.
*G01N 15/14* (2006.01)
*G01N 15/10* (2006.01)
*G06K 9/00* (2006.01)
*G01N 33/49* (2006.01)

(52) U.S. Cl.
CPC ............... *G01N 15/14* (2013.01); *G01N 15/10* (2013.01); *G01N 33/4915* (2013.01); *G06K 9/00536* (2013.01); *G01N 2015/1006* (2013.01); *G01N 2015/1402* (2013.01); *G01N 2015/1477* (2013.01); *G01N 2015/1488* (2013.01)

(58) Field of Classification Search
CPC .......... G01N 15/10; G01N 2015/1488; G01N 2015/1477; G01N 15/14; G01N 33/4915; G01N 2015/1402; G01N 2015/1006; G06K 9/00536
See application file for complete search history.

(56) References Cited

U.S. PATENT DOCUMENTS

| | | | |
|---|---|---|---|
| 4,661,913 A | 4/1987 | Wu et al. | |
| 6,263,337 B1 | 7/2001 | Fayyad | |
| 2002/0129038 A1 | 9/2002 | Cunningham | |
| 2007/0118297 A1* | 5/2007 | Thayer | ............................ 702/21 |
| 2010/0248362 A1 | 9/2010 | Durack et al. | |

(Continued)

FOREIGN PATENT DOCUMENTS

JP    2009-014355 A    1/2009

OTHER PUBLICATIONS

Kenneth Lo et al., "Automated Gating of Flow Cytometry Data via Robust Model-Based Clustering", Cytometry, Part A , 73A: pp. 321-332, 2008.*

(Continued)

*Primary Examiner* — Alexander Satanovsky
(74) *Attorney, Agent, or Firm* — Knobbe Martens Olson & Bear LLP

(57) ABSTRACT

The present invention provides automatic gating methods that are useful to gate populations of interest in multidimensional data, wherein the populations of interest are only a subset of the populations identifiable in the data. The populations are modeled as a finite mixture of multivariate probability distributions, preferably normal or t distributions. The distribution parameters that provide a best fit of the model distribution to the data are estimated using an Expectation Maximization (EM) algorithm that further includes a dynamic neighborhood thresholding that enables gating of a subset of the clusters present in the data.

10 Claims, 6 Drawing Sheets

(56) References Cited

U.S. PATENT DOCUMENTS

2011/0047448 A1* 2/2011 Bastos dos Santos
  et al. ............................. 715/227
2012/0245481 A1* 9/2012 Blanco et al. ................. 600/544

OTHER PUBLICATIONS

K.E. Basford et al. "Likelihood Estimation with Normal Mixture Models." Appl. Statist. vol. 34. No. 3:282-289 (1985).

A. Bashashati et al. "A survey of Flow Cytometry Data Analysis Methods." Handawi Publishing Corp. Advances in Bioinformatics. vol. 2009. Article ID 584603:1-19 (2009).

Baudry et al. Combining Mixture Components for Clustering. Technical Report No. 540. Department of Statistics. University of Washington. 1-20 (2008).

M.J. Boedigheimer et al. "Mixture Modeling Approach to Flow Cytometry Data." Cytometry Part A. vol. 73A:421-429 (2008).

C. Chan et al. "Statistical Mixture Modeling for Cell Subtype Identification in Flow Cytometry." Cytometry Part A. vol. 73A:693-701 (2008).

Kenneth Lo et al. "Automated Gating of Flow Cytometry Data via Robust Model-Based Clustering." Cytometry Part A. 73A:pp. 321-332. 2008. http://onlinelibrary.wiley.com/doi/10.1002/cyto.a.20531/pdf.

K. Lo et al. "flowClust: a Bioconductor package for automated gating of flow cytometry data." BMC Bioinformatics. vol. 10:145 (2009).

D. Peel et al. "Robust mixture modelling using the t distribution." Statistics and Computing. vol. 10:339-348 (2000).

Supplementary European Search Report for European Application No. EP 12 76 1433 dated Aug. 22, 2014.

* cited by examiner

(Con'd)

*(Con'd)*

*(Con'd)*

NEIGHBORHOOD THRESHOLDING IN MIXED MODEL DENSITY GATING

CROSS-REFERENCE TO RELATED APPLICATIONS

This specification is a continuation of and claims a benefit of priority to U.S. patent application Ser. No. 13/053,109 filed Mar. 21, 2011, now U.S. Pat. No. 8,990,047. The disclosure of the above-identified application is hereby expressly incorporated by reference in its entirety. Any and all priority claims identified in the Application Data Sheet, or any correction thereto, are hereby incorporated by reference under 37 C.F.R. §1.57.

BACKGROUND OF THE INVENTION

1. Field of the Invention

The present invention relates generally to methods for locating clusters in multidimensional data. The present invention is particularly applicable to identifying clusters corresponding to populations of cells or particles in data generated by cytometry, more particularly, flow cytometers.

2. Description of the Related Art

Particle analyzers, such as flow and scanning cytometers, are well known analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection, and a multiplicity of different particles or components may be simultaneously detected by using spectrally distinct fluorescent dyes to label the different particles or components. Typically, a multiplicity of photodetectors, one for each of the scatter parameters to be measured, and one for each of the distinct dyes to be detected. The data obtained comprise the signals measured for each of the light scatter parameters and the fluorescence emissions.

Cytometers further comprise means for recording the measured data and analyzing the data. For example, typically, data storage and analysis is carried out using a computer connected to the detection electronics. The data typically are stored in tabular form, wherein each row corresponds to data for one particle, and the columns correspond to each of the measured parameters. The use of standard file formats, such as an "FCS" file format, for storing data from a flow cytometer facilitates analyzing data using separate programs and machines. Using current analysis methods, the data typically are displayed in 2-dimensional (2D) plots for ease of visualization, but other methods may be used to visualize multidimensional data.

The parameters measured using a flow cytometer typically include the excitation light that is scattered by the particle along a mostly forward direction, referred to as forward scatter (FSC), the excitation light that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described at length in the extensive literature in this field, including, for example, Landy et al. (eds.), Clinical Flow Cytometry, Annals of the New York Academy of Sciences Volume 677 (1993); Bauer et al. (eds), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Shapiro, Practical Flow Cytometry, 4th ed., Wiley-Liss (2003); all incorporated herein by reference. Fluorescence imaging microscopy is described in, for example, Pawley (ed), Handbook of Biological Confocal Microscopy, 2nd Edition, Plenum Press (1989), incorporated herein by reference.

The data obtained from an analysis of cells (or other particles) by multi-color flow cytometry are multidimensional, wherein each cell corresponds to a point in a multidimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots, of the data. Alternatively, clusters can be identified, and gates that define the limits of the populations, can be determined automatically. A number of methods for automated gating have been described in the literature. See, for example, U.S. Pat. Nos. 4,845,653; 5,627,040; 5,739,000; 5,795,727; 5,962,238; 6,014,904; 6,944,338, each incorporated herein by reference.

Mixed model approaches to identifying clusters in data that correspond to populations have been described. A mixed model approach to clustering is based on modeling the data as a finite mixture of distributions, in which each component distribution is taken to correspond to a different population. Most commonly, the component distributions are assumed to be a multivariate Gaussian (normal) distributions or t distributions. One methodology for fitting the mixture of distributions to the data consists of using an expectation-maximization (EM) algorithm to estimate the parameters of the distributions corresponding to the clusters. Each event (data from a single cell or particle) is classified as a member of the population cluster to which it is most likely to belong. The use of multivariate mixture modeling for the gating of data generated by flow cytometry has been described in, for example, Boedgheimer et al., Cytometry 73A: 421-429, 2008; Chan et al., Cytometry 73A: 693-701, 2008; and Lo et al., Cytometry 73A: 321-332, 2008, each incorporated herein by reference. More generally, the use of pattern recognition to identify populations is described in Boddy et al., Cytometry 44:195-209, 2001, incorporated herein by reference.

SUMMARY OF THE INVENTION

The present invention provides automatic gating methods that are useful for gating clusters or populations in multidimensional data. The methods are particularly applicable to identifying populations of cells or particles in multidimensional flow cytometry data. The present methods enable the specific gating of populations of interest that are only a subset of the populations identifiable in the data, as is the case in many flow cytometry applications.

In the methods of the present invention, the data are modeled as a finite mixture of parametric distributions, in which each component distribution is taken to correspond to a different population. Thus, each population of interest, recognized as a cluster in the data, is modeled by a multivariate probability distribution, preferably a multivariate normal or t distribution. The distribution parameters that provide a best fit of the distributions to the data are estimated from the data. After the parameters have been estimated for each distribution corresponding to a population of interest, a gate defining the limits of a particular population is then determined based on the distribution.

The distribution parameters that provide a best fit of the model distributions to the data are estimated using an Expectation Maximization (EM) algorithm that further includes a neighborhood thresholding to enable gating of a subset of the clusters present in the data.

The EM algorithm is an iterative optimization method for estimating unknown parameters given measurement data. The EM process alternates between an expectation step ("E-step") and a maximization step ("M-step"). The E-step, described more fully below, updates the a posteriori probability of each event associated with each component, given the model parameters. The M-step updates the model parameters, given the a posteriori probabilities of all events. The process is repeated until the model parameter estimates have converged to a desired degree. The EM algorithm (without the improvements of the present invention) is well known and has been described extensively in the literature. For example, see Basford and McLachlan, Appl. Statist. 34(3):282-289, 1985; Peel and McLachlan, Statistics and Computing 10:339-348, 2000; Boedgheimer et al., Cytometry 73A: 421-429, 2008; Chan et al., Cytometry 73A: 693-701, 2008; and Lo et al., Cytometry 73A: 321-332, 2008, each incorporated herein by reference.

In the EM process of the present invention, the M-step, described more fully below, updates the model parameters, given the a posteriori probabilities of only a subset of the events. The updating of the parameter estimates of a distribution in the M-step are carried out using only the data from events that fall within a neighborhood of at least one of the model distributions. The neighborhood of a distribution is defined by a predefined threshold distance from the center of the distribution, which distance depends on the distribution parameters that were estimated in the previous M-step. In preferred embodiments, the neighborhood is defined such that all events that satisfy a threshold criterion of a function of the squared Mahalanobis distance are identified as within the neighborhood of the distribution. More particularly, in some embodiments, the neighborhood is defined such that all events whose squared Mahalanobis distance from a distribution is less than a predetermined threshold value are identified as within the neighborhood of the distribution. The neighborhood is calculated dynamically, based on the distribution parameters that are updated during each M-step.

In many flow cytometry applications, the populations of interest are only a subset of the populations identifiable in the data. For example, a typical flow cytometry assay is used to provide an enumeration of cells in one or more specific populations, but the rest of the types of cells in the sample (e.g., of blood) are ignored. The present methods are particularly applicable in such applications because only the populations of interest are modeled by fitting a distribution to the data, the other populations are ignored. The exclusion of any events outside the neighborhood of any of the model distributions, carried out using the dynamically calculated neighborhood thresholding, when updating the parameter estimates enables effectively modeling only one or a subset of the total number of population clusters present in the data set.

In contrast to the present methods, in previously described mixed model methods based on the EM methodology, all data is considered when updating the parameter estimates. Using the prior EM methods, if the number of clusters in the data is greater than the number of distributions included in the model, the parameter estimates may be compromised by data from events that are far away from the model distributions corresponding to populations of interest and which probably do not actually belong to one of the modeled clusters, and the resulting final results can be inaccurate. The EM methods of the present invention overcome this limitation and enable modeling of a subset of the total number of population clusters present in the data set.

Typically, the number of distinct cell populations identifiable in a data set is known from experience and predictable from the selection of the fluorescence antibodies used to label the cells. Gating methods then are used to identify the limits of the populations to enable accurate enumeration of the cells in each population, rather than to identify a previously unknown population. It is assumed in the present methods that the number of populations of interest is a known parameter, whereas the total number of populations identifiable in the data need not be known due to the neighborhood thresholding that is used to ignore events that are not in the neighborhood of any of the modeled populations. However, the number of populations also can be estimated from the data, either by visual inspection or by using algorithmic data analysis methods. Methods of estimating the number of clusters in a set of data are known in the art, and can be applied in the present methods to obtain the number of cell populations to be gated.

The present methods are particularly suited for use in applications wherein an assay is applied repetitively to numerous similar samples, such as, for example, for use in a diagnostic assay that is carried out on samples from many patients. In this case, the data from each patient are typically very similar, and the cell populations observed within the sample will consistently be observed in similar positions within a data plot. However, due both to differences between patients (and patient health) and differences between instruments or instrument settings, the exact positions and boundaries of the cell populations typically differ. The present methods are useful to optimally identify the location and boundaries of the populations of interest for each patient sample.

Suitable initial parameters for the model distributions, which correspond to the location and shape of each distribution, can be estimated from a prior analysis of similar or typical samples. For example, training samples can be analyzed using the present methods, starting with some approximated initial parameter values, and the final estimated parameter values can be used as initial parameters to start the EM process for future assays. Alternatively, the estimates of appropriate initial parameter values can be updated for use in future assays based on past performance. Preferably, some statistical measure of the typical parameter values obtained, such as the mean of a parameter estimated from a number of samples, is used as the initial parameter value for future assays. It is desirable to use initial parameter values that are likely to be close to the final estimated values in order to minimize the number of iterations required by the EM process to obtain the desired convergence.

Thus, in one aspect, the present invention provides methods of gating a number, G, of clusters in p-dimensional data that contain at least G clusters, wherein the data are obtained from measurements of a set of N events, comprising:

a) modeling the data using a mixture of G p-dimensional parametric distributions;

b) providing an initial estimate of the parameters of said p-dimensional parametric distributions;

c) estimating updated parameters for each of the p-dimensional parametric distributions functions using an iterative Expectation Maximization (EM) algorithm, wherein said EM process comprises the steps of:

i) calculating, for each event, a posteriori probabilities that said event is a member of each of the parametric distributions, ii) identifying a subset, I, of the events that are within a neighborhood of at least one of said distributions, iii) calculating, for each of the parameters, an updated estimate, given the a posteriori probabilities from step i) for each of the events in subset I, wherein said EM algorithm is iterated at least once; and d) identifying a gate from each of the distributions using the updated parameter estimates.

In preferred embodiments, an event is defined to be within a neighborhood of a distribution if a monotonic function of the squared Mahalanobis distance of the event from the distribution satisfies a predefined threshold condition. Preferably, the p-dimensional parametric distributions are p-dimensional Gaussian distributions or t-distributions.

In another aspect, the present invention provides a system capable of using the present methods to identify clusters in multidimensional data. In a preferred embodiment, the system is a flow cytometer system that includes both the flow cytometer and a computer that carries out the data analysis.

DETAILED DESCRIPTION OF THE PREFERRED EMBODIMENT

Figure 1:
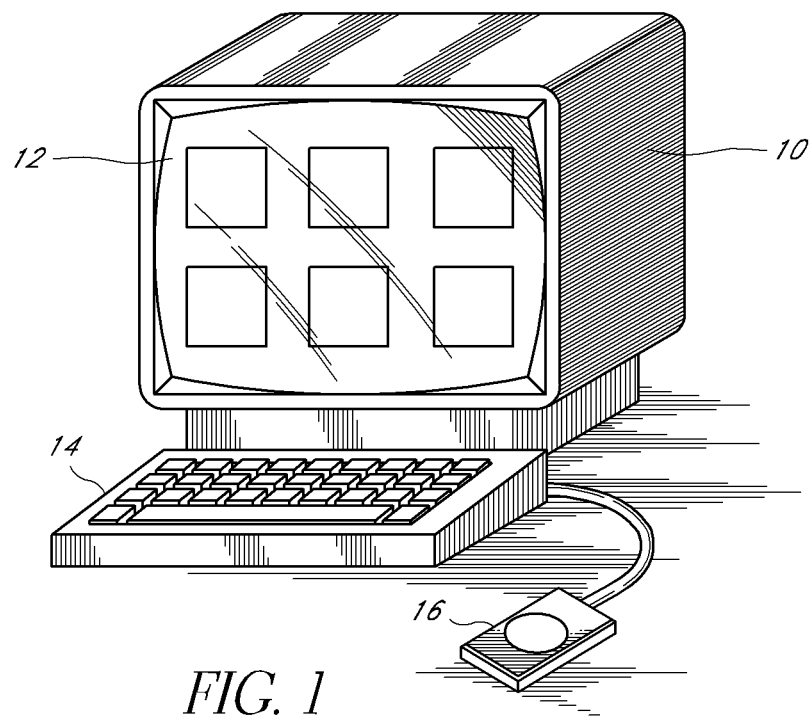
FIG. 1 is a perspective view of an embodiment of a computer console and display screen useful for carrying out the method of the present invention for analyzing multi-parameter data.

The following definitions are provided for clarity. Unless otherwise indicated, all terms are used as is common in the art. All reference cited herein, both supra and infra, are incorporated herein by reference.

As used herein, "system" and "instrument" and "apparatus" are intended to encompass both the hardware (e.g., mechanical and electronic) and associated software (e.g., computer programs) components.

As used herein, an "event" refers to the data measured from a single particle, such as cells or synthetic particles). Typically, the data measured from a single particle include a number of parameters, including one or more light scattering parameters, and at least one fluorescence intensity parameters. Thus, each event is represented as a vector of parameter measurements, wherein each measured parameter corresponds to one dimension of the data space.

As used herein, a "population", or "subpopulation" of particles, such as cells or other particles, refers to a group of particles that possess optical properties with respect to one or more measured parameters such that measured parameter data form a cluster in the data space. Thus, populations are recognized as clusters in the data. Conversely, each data cluster generally is interpreted as corresponding to a population, although clusters that correspond to noise or background typically also are observed. A cluster may be defined in a subset of the dimensions, i.e., with respect to a subset of the measured parameters, which corresponds to populations that differ in only a subset of the measured parameters.

The term "MFI", as used herein, refers to the mean or median fluorescence intensity of a population of fluorescence particles. It will be understood that other statistical measures of the population fluorescence, such as truncated mean or truncated median fluorescence, may be used.

The data obtained using a flow cytometer to analyze particles or cells may be transformed to facilitate analysis or display. For example, the data may be shifted using a linear transformation to keep the data within the range of the dot plot. Alternatively, or additionally, the data may be rescaled using a non-linear transformation, such as, for example, a log transform, to keep the range of the data within the range of the dot plot. These optional data transformations also facilitate visually recognizing population clusters within the data when displayed. In practice, fluorescence intensity parameters typically are log-transformed or displayed on a log scale, and scatter parameters typically are displayed on a linear scale, each sometimes modified to facilitate the display of near-zero data. For example, the fluorescence MFI data typically are transformed to a log scale with base 10, and MFI values less than 1 are converted to 1 before the log transformation to avoid obtaining negative transformed data. Similarly, side scatter (SSC) data typically are displayed on a linear scale, and any event with a measured SSC value less than 0, which can result from noise in the detection system, is removed before gating. Parameters values typically are scaled to be in a standard range, e.g., (0, 1000).

The data from the cell or particle populations preferably are compensated prior to carrying out analysis using the present methods, although this is not a critical aspect of the invention and the present methods can be used with uncompensated or partially compensated data. Compensation is useful for data obtained using an instrument that measures emissions from multiple dyes using multiple photodetectors, each photodetector configured to detect emissions from one of the dyes, such as a typical flow cytometer. Compensation refers to the process of effectively removing from the total amount of light detected by a photodetector the contribution due to spillover emissions from dyes other than the intended dye. Thus, after compensation, the amount of light detected from a single photodetector represents a measure of the light emitted by a single dye. Compensation facilitates analysis of the data from multiply dyed particles by making the measurements of each of the dyes independent. Methods of compensation are known in the art and are described in, for example, Bagwell et al. "Fluorescence Spectral Overlap Compensation for any Number of Flow Cytometer Parameters", Ann. N.Y. Acad. Sci. 677, 167-184 (1993); Roederer et al., "Eight Color, 10-Parameter Flow Cytometry to Elucidate Complex Leukocyte Hetrogeneity", Cytometry 29, 328-339 (1997); and Bigos et al., Cytometry 36: 36-45 (1999), each incorporated herein by reference. WinList™ (Verity Software House, Topsham, Me.) is a stand-alone software package that allows software compensation on the stored data files produced by a flow cytometer. See also the whitepaper describing the BD FACSDiVa™ Option for the BD FACS Vantage SE Flow cytometer (available from BD Biosciences, San Jose, Calif.), incorporated herein by reference.

Having obtained and stored the data about the cell sample under analysis, different formatting techniques may be employed to analyze the data. Use of computer programs, microprocessors and display consoles is common and well-known for the refinement or analysis of flow cytometric data. As seen in FIG. 1, a monitor 10 is provided for displaying the data on a CRT screen 12 for visualization by the person undertaking the analysis. A keyboard 14 permits the user to access the data in the format chosen to store the data. In the embodiment illustrated, a mouse 16 is preferably included so that the cursor, as described below, applied to screen 12 may be electronically moved across the screen by hand manipulation of the mouse by the user, in a fashion well-known to those skilled in the art.

It is appreciated that the data obtained by the flow cytometric techniques may be displayed or formatted in many different forms, as may be desirable or feasible for the type of analysis contemplated. The computer program or algorithm may be devised to show the data in graphs, charts and, preferably, for purposes of the present invention, in different color schemes (it being assumed that monitor 10 has color capabilities). In the display of FIG. 1 which includes multiple data fields, cell type or cell subpopulation differentiation may be provided either directly by the user or by pattern recognition or cluster analysis or other heuristic or mathematical techniques so that it is possible to analyze, detect or identify such differentiated cells in a single viewing of the display screen. It should be noted, however, that the present invention is limited to viewing data on a single screen, since there are instances when all the desired data may not fit on a single screen. Multiple screens may be used or linked for the simultaneous display of large amounts of data. Alternatively, one screen may be programmed to display data of different types on a sequential or rotating basis, if desired or necessary.

The present methods are general gating methods that can be applied to the gating of any cell population whose distribution can be approximated using a parametric probabilistic distribution. Each population, which is identified as a cluster in the data, is modeled by a multivariate probability distribution.

In preferred embodiments, the clusters to be modeled are modeled by multivariate probability distributions having the same distribution, differing only by the parameter values. For example, the clusters of interest within the data may be modeled using a mixture of Gaussian distributions, wherein the mean vector and covariance matrix of each distribution is estimated to fit the distribution to one of the populations. Preferred distributions for use in gating cell population data obtained using flow cytometry include Gaussian (normal) distributions and t-distributions.

The number of populations to be modeled is assumed to be a known parameter. Typically, the number of distinct cell populations identifiable in a data set is known from experience and predictable from the selection of the fluorescence antibodies used to label the cells. Furthermore, the number of cell populations of interest for the particular application may be a subset of the total number of distinct cell populations identifiable in a data set. The number of populations to be modeled will typically be limited to the populations of interest, but may include additional populations, if present.

The data (set of events) to be analyzed, y, comprise independent multivariate observations $y_1, y_2, \ldots, y_N$, where each observation is a p-dimensional vector of measured parameter values, and N is the total number of events. The data are modeled using a finite mixture of multivariate probability distributions, wherein each population preferably is described by a separate distribution. The number of populations to be modeled is assumed to be a known parameter, G, which may be less than the number of clusters identifiable in the data. Thus, the set of events, y, is modeled by a mixture of G components, each component corresponding to one of the populations of interest.

Gaussian Distributions

In a preferred embodiment, each component is modeled by a multivariate Gaussian (normal) distribution. The likelihood, l, for a mixture model with G components, given data y, is:

$$l(\mu_1, \ldots, \mu_G; \Sigma_1, \ldots, \Sigma_G; w_1, \ldots, w_G \mid y) = \prod_{i=1}^{N} \sum_{g=1}^{G} w_g \phi_p(y_i \mid \mu_g, \Sigma_g), \quad (1)$$

$$\sum_{g=1}^{G} w_g = 1, \quad (2)$$

where $\phi_p(\bullet \mid \mu_g, \Sigma_g)$ is the p-dimensional multivariate Gaussian distribution with mean $\mu_g$ and covariance matrix $\Sigma_g$, and $w_g$ is the probability that an observation belongs to the gth component. In the preferred embodiment in which each component is modeled by a multivariate normal distribution, the probability density function (pdf) is:

$$\phi_p(y_i \mid \mu_g, \Sigma_g) = (2\pi)^{-p/2} |\Sigma_g|^{-1/2} \exp\{-(y_i - \mu_g)^T \Sigma_g^{-1} (y_i - \mu_g)/2\}. \quad (3)$$

The present methods typically are used to gate two-dimensional data, as displayed in a two-dimensional dot-plot, also referred to as a scatter-plot. For two-dimensional data, the mean $\mu_g$ of each population is a 1×2 vector and the covariance matrix $\Sigma_g$ of each population is a 2×2 matrix.

Estimates of the unknown parameters, $\mu_g$, $\Sigma_g$, and $w_g$, are obtain using the modified expectation-maximization (EM) iterative optimization process of the present invention, as described more fully, below. After the parameters values have been estimated, the gates (boundaries) for one or multiple populations in the sample are determined based on the model distributions, evaluated with the final parameter values, and the events that fall within each are identified and, optionally counted.

The expectation-maximization (EM) iterative optimization process of the present invention is used to estimate the parameters of a parametric distribution function by fitting the distribution to a set of data. The iterative EM process is repeated, alternating between an E-step and an M-step, until the parameter estimates converge.

E-step updates the a posteriori probability of each event associated with each component, given the model parameters.

$$\tilde{z}_{ig} \leftarrow \frac{w_g \Phi_p(y_i \mid \mu_g, \Sigma_g)}{\sum_{j=1}^{G} w_j \Phi_p(y_i \mid \mu_j, \Sigma_j)}, \quad (4)$$

where $\tilde{z}_{ig}$ is the a posteriori probability of event i associated with component g, i.e., the a posteriori probability that event $y_i$ belongs to cluster g.

The M-step updates the model parameters, given the a posteriori probabilities of the events. In the present methods, only events within a neighborhood of a cluster that is being modeled (i.e., a population of interest) are considered for updating the model parameters. Events that are not in a neighborhood of any of the clusters are ignored. This allows the present methods to ignore events associated with clusters that are not of interest or are background noise, and thus allows the present methods to model a subset of the clusters identifiable in the data.

An event is considered to be within a neighborhood of a distribution if the squared Mahalanobis distance is less than a predetermined threshold. The squared Mahalanobis distance of an event, $y_i$, with respect to a model component distribution, g, is:

$$D_{ig} = (y_i - \mu_g)^T \Sigma_g^{-1} (y_i - \mu_g), \quad (5)$$

where $\mu_g$ and $\Sigma_g^{-1}$ are the mean vector and inverse of the covariance matrix, $\Sigma$, respectively, for model component distribution g.

An event is used in the M-step if the event is within the neighborhood of at least one of component distributions, i.e., if the minimum of the distances $D_{ig}$, across all distributions, is less than a predetermined threshold value, T. Let $D_i^*$ be the minimum of the distances $D_{ig}$, across all distributions, $$D_i^* \leftarrow \min\{D_{ig}, g=1,2,\ldots G\}, \quad (6)$$

where G is the number of populations being modeled.

Then, the set of inlier events for the current iteration of the EM process, designated I, is defined as:

$$I \leftarrow \{y_i | D_i^* < T, i=1,2,\ldots,N\} \quad (7)$$

The M-step updates the model parameters (a carat over a parameter symbol is used herein to indicate an updated parameter) according to the following formulas, in which the summations are over the set of inliers, I:

$$\hat{\mu}_g \leftarrow \frac{\sum_{i \in I} \hat{z}_{ig} y_i}{\sum_{i \in I} \hat{z}_{ig}} \quad (8)$$

$$\hat{\Sigma}_g \leftarrow \frac{\sum_{i \in I} \hat{z}_{ig}(y_i - \hat{\mu}_g)(y_i - \hat{\mu}_g)^T}{\sum_{i \in I} \hat{z}_{ig}} \quad (9)$$

$$\hat{w}_g \leftarrow \frac{1}{n_I} \sum_{i \in I} \hat{z}_{ig}, \quad (10)$$

where $n_I$ is the total number of inliers in set I.

t Distributions

In an alternative preferred embodiment, each component is modeled by a multivariate t distribution. Experiment results show that a mixture of t distribution components can give improved results when modeling clusters in data that include significant noise, which often is observed in flow cytometry data. The likelihood, l, for a mixture model with G components, given data y, is:

$$l(\mu_1, \ldots, \mu_G; \Sigma_1, \ldots, \Sigma_G; w_1, \ldots, w_G | y, v) = \quad (11)$$

$$\prod_{i=1}^{N} \sum_{g=1}^{G} w_g \varphi_p(y_i | \mu_g, \Sigma_g, v)$$

$$\sum_{g=1}^{G} w_g = 1, \quad (12)$$

where $\phi_p(\cdot | \mu_g, \Sigma_g)$ is the p-dimensional multivariate t distribution with mean $\mu_g$, covariance matrix $\Sigma_g$, v is the number of degree of freedom, and $w_g$ is the probability that an observation belongs to the gth component. The probability density function (pdf) of a multivariate t distributions is:

$$\varphi_p(y_i | \mu, \Sigma, v) = \frac{\Gamma\left(\frac{v+p}{2}\right)}{\pi^{p/2} |\Sigma|^{1/2} v^{p/2} \Gamma\left(\frac{v}{2}\right) \{1 + (y_i - \mu)^T \Sigma^{-1}(y_i - \mu)/v\}^{\frac{v+p}{2}}} \quad (13)$$

where $\Gamma$ is the gamma function.

The present methods typically are used to gate two-dimensional data, as displayed in a two-dimensional dot-plot, also referred to as a scatter-plot. For two-dimensional data, the mean $\mu_g$ of each population is a 1×2 vector and the covariance matrix $\Sigma_g$ of each population is a 2×2 matrix. For two-dimensional data (p=2), the pdf of the t distribution reduces to:

$$\varphi_2(y_i | \mu, \Sigma, v) = \frac{1}{2\pi \sqrt{|\Sigma|} \{1 + (y_i - \mu)^T \Sigma^{-1}(y_i - \mu)/v\}^{(v+2)/2}}. \quad (14)$$

Typically, the number of degrees of freedom, v, is assumed to be a known constant. A value of v=2 has been found to be useful for the gating of experimental data. In general, the number of degrees of freedom is not a critical aspect of the invention. As is well known, as the number of degrees of freedom increases, a t distribution converges to a Gaussian distribution. Thus, for higher degrees of freedom, the results obtained using the present methods with t distributions will be essentially identical to results obtained using the present methods with Gaussian distributions.

The EM process of the present invention wherein the model distributions are t distribution is carried out essentially as described above for models of Gaussian distributions. Preferred calculations are described below for use with t distributions in which a weight parameter, $\tilde{u}_{ig}$, is defined (see Equation 16). The E-step updates both the posterior probability $\tilde{z}_{ig}$ and the weight $\tilde{u}_{ig}$ of each event associated with each component distribution.

$$\tilde{z}_{ig} \leftarrow \frac{w_g \varphi_p(y_i | \mu_g, \Sigma_g, v)}{\sum_{j=1}^{G} w_j \varphi_p(y_i | \mu_j, \Sigma_j, v)}, \quad (15)$$

where $\tilde{z}_{ig}$ is the posterior probability of event i associated with component g.

$$\tilde{u}_{ig} \leftarrow \frac{v+p}{v + (y_i - \mu_g)^T \Sigma_g^{-1}(y_i - \mu_g)}, \quad (16)$$

where $\tilde{u}_{ig}$ is the weight of event i with respect to component g.

As described above, only events within a neighborhood of a cluster that is being modeled (populations of interest) are considered for updating the model parameters. Events that are not in a neighborhood of any of the clusters are ignored. A neighborhood of a model distribution can be defined based directly on the squared Mahalanobis distance, as described above. Clearly, however, a neighborhood can be defined equivalently using any monotonic function of the squared Mahalanobis distance, using an appropriate threshold. The weight parameter, $\tilde{u}_{ig}$, as defined, is a function of the squared Mahalanobis distance of event i with respect to distribution g, albeit the weight parameter is inversely related to the squared Mahalanobis distance. Thus, a neighborhood of a distribution can be defined equivalently by a threshold on the weight parameter, wherein any event having a weight parameter greater than the threshold is classified as within the neighborhood of the distribution.

An event is used in the M-step if the event is within the neighborhood of at least one of component distributions, which is true if the maximum of the weights $\tilde{u}_{ig}$, across all distributions, is greater than a predetermined threshold value, T. Let $\tilde{u}_i^*$ be the maximum of the weights $\tilde{u}_{ig}$ across all distributions, $$\tilde{u}_i^* \leftarrow \max\{\tilde{u}_{ig}, g=1,2,\ldots G\} \tag{17}$$

where G is the number of populations being modeled.

Then, the set of inlier events for the current iteration of the EM process, designated I, is defined as:

$$I \leftarrow \{y_i | \tilde{u}_i^* > T, i=1,2,\ldots,N\} \tag{18}$$

The M-step updates the model parameters according to the following formulas, in which the summations are over the set of inliers, I:

$$\hat{\mu}_g \leftarrow \frac{\sum_{i \in I} \tilde{z}_{ig} \tilde{u}_{ig} y_i}{\sum_{i \in I} \tilde{z}_{ig} \tilde{u}_{ig}} \tag{19}$$

$$\hat{\Sigma}_g \leftarrow \frac{\sum_{i \in I} \tilde{z}_{ig} \tilde{u}_{ig} (y_i - \hat{\mu}_g)(y_i - \hat{\mu}_g)^T}{\sum_{i \in I} \tilde{z}_{ig}} \tag{20}$$

$$\hat{w}_g \leftarrow \frac{1}{n_I} \sum_{i \in I} \tilde{z}_{ig}, \tag{21}$$

where $n_I$ is the total number of inliers in set I.

In general, the EM process of the present invention will begin with an E-step, wherein initial model parameters are provided as a starting point. The process is repeated until the models have suitably converged. The degree of convergence can be measured by comparing the difference between two estimated distributions obtained in consecutive iterations, and comparing the difference to a preselected "tolerance" parameter. If the difference between iterations is less that the tolerance parameter, then the process is halted and the estimated parameter values are used as the final value for the determination of the gate boundaries. The convergence criterion for the EM algorithm for a mixture model is usually defined in terms of the change of the logarithm of the likelihood between two consecutive iterations. However, any measure of the distributions that converges along with the parameter convergence can be used by looking at the difference in the measure between iterations and stopping the EM process if the change is less than a predefined tolerance.

Preferably, the EM process of the present invention is initialized using model parameters that were obtained from the prior analysis of a test sample or experience. Much flow cytometry analysis consists of repeated applications of an assay on different samples, such as when running a diagnostic test on multiple patients. In most cases, it is expected that the results obtained from previous patient samples will be similar to the results that will be obtained from the patient sample to be analyzed, and the parameter values estimated from the previous patient samples provide preferred initial values for the EM process. The use of previously estimated parameters as the initial parameter values greatly speeds up the processing time required to estimate the final parameter values.

Once the final distribution parameters are determined using the algorithm described above, a final gating preferably is carried out based on the final distributions. Boundaries of the final gates, which define the set of events that are identified as members of a population, can be obtained by thresholding on the squared Mahalanobis distances of all events calculated based on the final parameters. Typically, a more relaxed (e.g., larger) threshold value is used so that the final gate in more inclusive of events. However, if high specificity of results is desirable, the final gate may be rendered more restrictive by using a more stringent threshold value. For modeling with bivariate Gaussian or t distributions, the shape of the final gate will be an ellipse. Alternatively, other final gate definitions can be used, such as using a contour level obtained from a final distribution. The final gates will be determined from the final distributions, although the particular definition of the final gates is not a critical aspect of the invention.

The following example is put forth so as to provide one of ordinary skill in the art with a complete disclosure and description of how to make and use the present invention, and is not intended to limit the scope of what the inventors regard as their invention.

EXAMPLE 1

Gating of a Single Population

The present methods were used to gate data obtained using the BD TriTEST™ CD3 fluorescein isothiocyanate (FITC)/CD4 phycoerythrin (PE)/CD45 peridinin chlorophyll protein (PerCP) reagents, essentially following the manufacturers protocols (BD Biosciences, San Jose, Calif.).

FIG. 1 shows the gating of a single cell population, specifically CD45+ leukocytes, in a two-dimensional dot-plot of the fluorescence intensity measured from cells stained with PerCP-labeled anti-CD45 antibodies (axis labeled "PerCP") plotted against side scatter (SSC). The EM process converged after 6 iterations. The gates shown in each of the iterations, which are shown as solid grey ellipses positioned over the event data shown in black, correspond to the dynamic neighborhood threshold applied in each M-step. The final gate shown in last plot as a larger ellipse was obtained using a more relaxed threshold.

Figure 2:
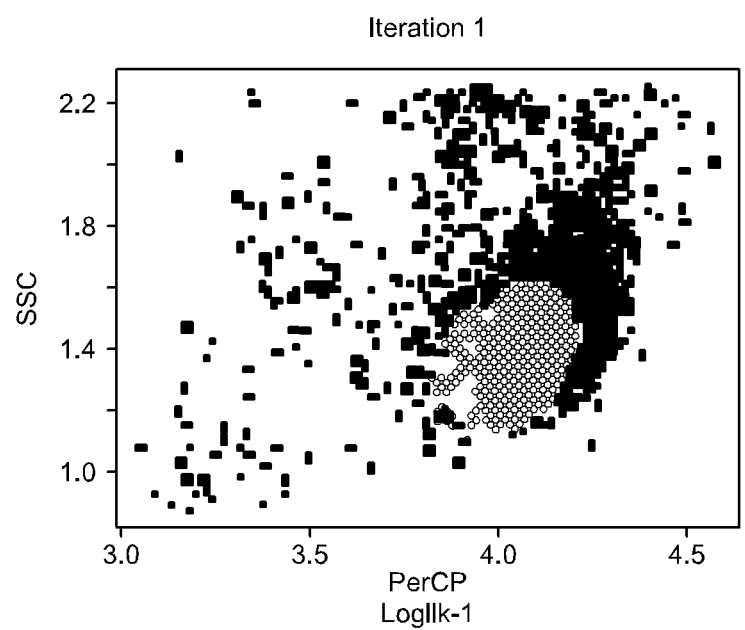
FIG. 2 illustrates the application of the gating methods of the present invention to gate data corresponding to a single cell population in a sample of blood, as described in Example 1.
Figure 2:
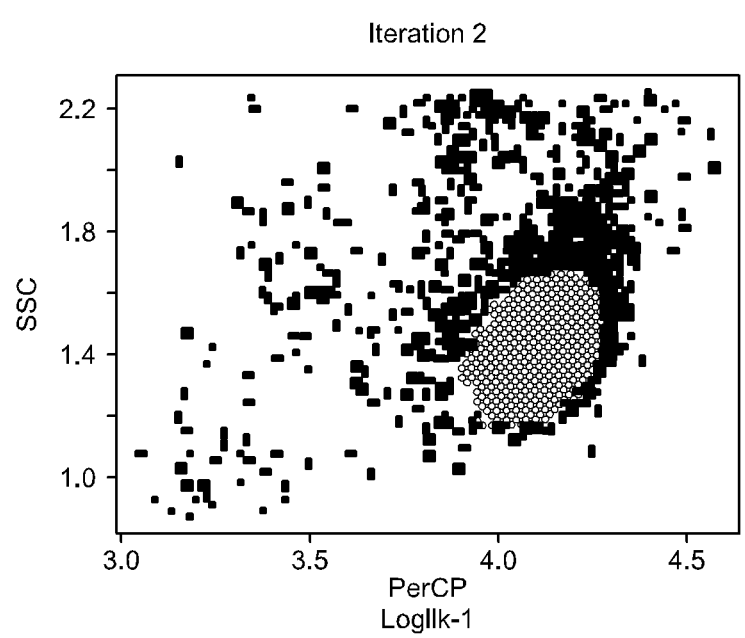
Figure 2:
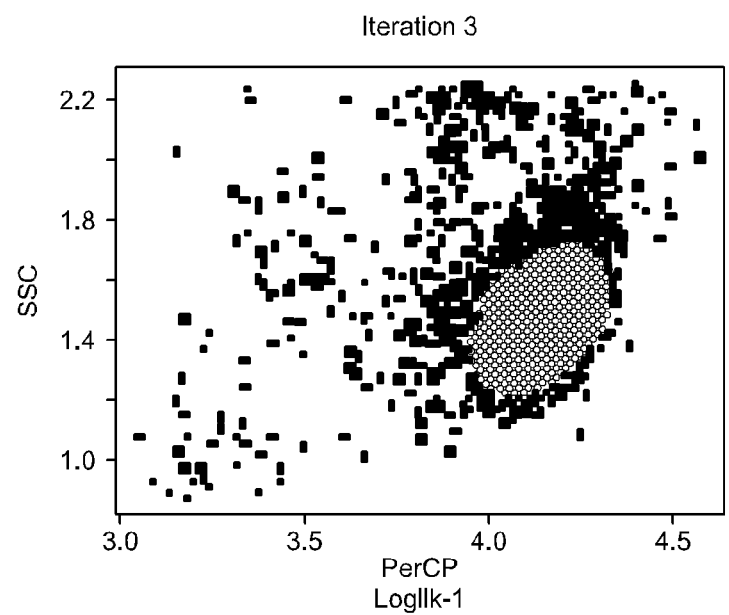
Figure 2:
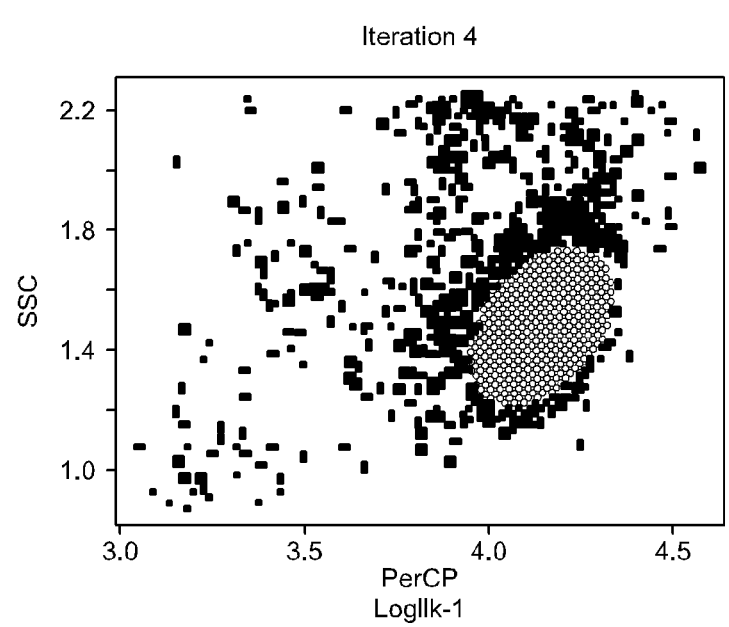
Figure 2:
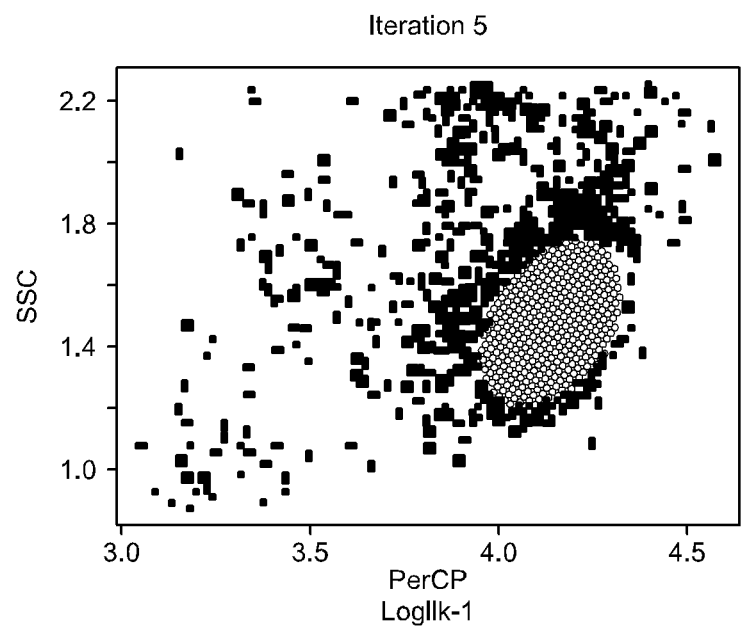
Figure 2:
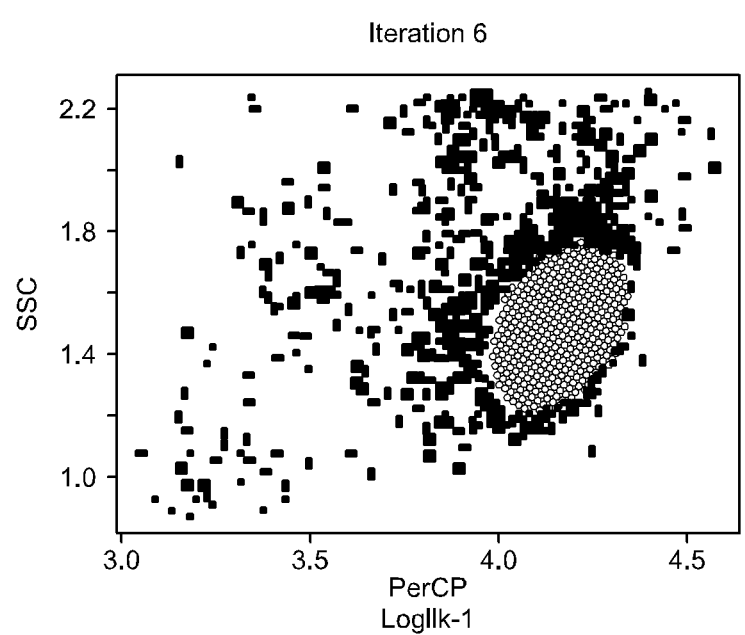
Figure 2:
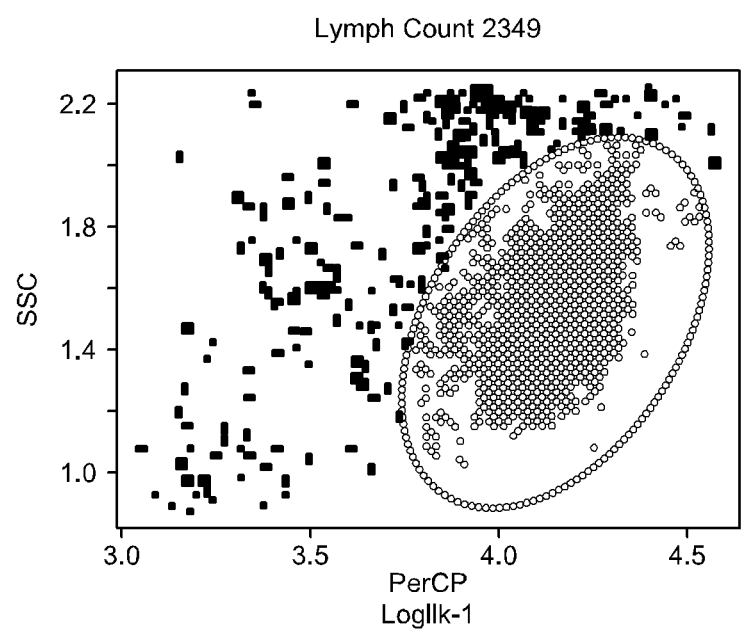
Figure 3:
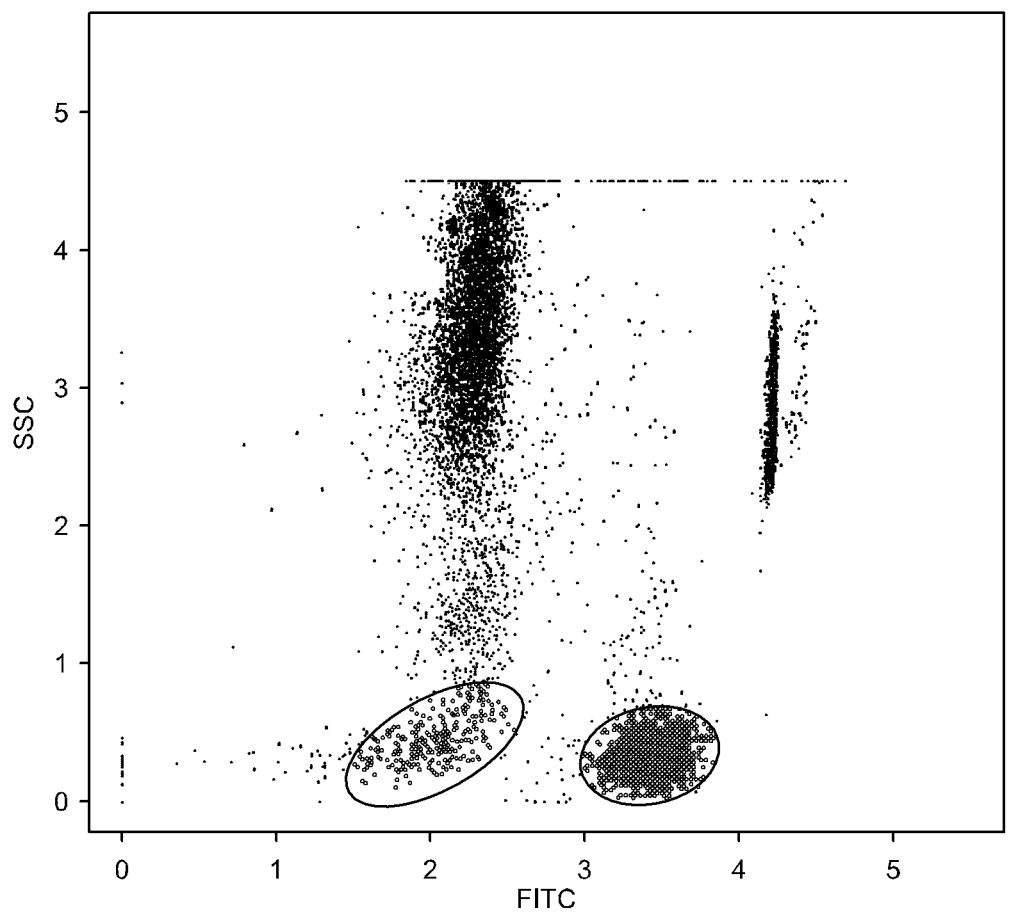
FIG. 3 shows results of using the gating methods of the present invention to gate data corresponding to two cell populations in a sample of blood, as described in Example 1.

FIG. 2 shows the final gate obtained for two populations, CD3+ and CD3− lymphocytes, in a two-dimensional dot-plot of the fluorescence intensity measured from cells with FITC-labeled anti-CD3 antibodies (axis labeled "FITC") plotted against side scatter (SSC). As can be readily seen, the dot-plot contains a number of recognizable clusters, and the present methods were used to gate only a subset of the clusters present in the data.

What is claimed is:
1. A system for performing computer aided flow cytometry experiments, the system comprising:
   a flow cytometer;
   a data storage configured to store measurements of a set of cytometric events for particles in a sample subjected to a flow cytometric experiment in the flow cytometer, the measurements including p-dimensional data;
   a processor in data communication with the data storage, the processor configured to:
      obtain the measurements;
      model at least a portion of the p-dimensional data included in the measurements based on one or more p-dimensional parametric distributions;

provide an initial estimate of parameters included in said one or more p-dimensional parametric distributions;

iteratively estimate updated parameters for said one or more p-dimensional parametric distributions, wherein said estimating comprises:

calculating, for events in the set of cytometric events, a posteriori probabilities that said event is a member of each of said parametric distributions, calculating, for said events, distances that said event to said parametric distributions, identifying a subset of said events that are within a neighborhood of at least one of said distributions based on a comparison of the calculated event distance for a respective parametric distribution with a predefined threshold, and calculating, for the parameters for the said one or more p-dimensional parametric distributions, an updated estimate based on the calculated a posteriori probabilities for events in the identified subset of said events, wherein said estimating is iterated at least once, and wherein subsequent calculation of the a posteriori probabilities is based on the updated estimate for the parameters; and after said iterative estimating, identify a gate indicating a population of particles from the said one or more p-dimensional parametric distributions using the updated parameter estimates.

2. The system of claim 1, further comprising a display configured to present a two-dimensional plot of the measurements in conjunction with the gate.

3. The system of claim 1, wherein an event is defined to be within a neighborhood of a distribution if a monotonic function of the squared Mahalanobis distance of the event from the distribution satisfies a predefined threshold condition.

4. The system of claim 3, wherein said p-dimensional parametric distributions functions are p-dimensional Gaussian distributions.

5. The system of claim 4, wherein an event is defined to be within a neighborhood of a distribution function based on a comparison of the squared Mahalanobis distance of the event from a distribution and a predefined threshold.

6. The system of claim 3, wherein said p-dimensional parametric distributions functions are p-dimensional t distributions.

7. The system of claim 6, wherein an event is defined to be within a neighborhood of a distribution function based on a comparison of a weight of the event with respect to a model distribution component and a predefined threshold.

8. The system of claim 1, wherein said estimating is iterated two times.

9. The system of claim 1, wherein the center point of a distribution is determined based on a shape of the distribution.

10. The system of claim 9, wherein the shape is provided as a variance-covariance matrix for the distribution.

* * * * *